(12) United States Patent
Strauss et al.

(10) Patent No.: US 9,549,265 B2
(45) Date of Patent: Jan. 17, 2017

(54) METHODS AND SYSTEMS FOR ENHANCING PITCH ASSOCIATED WITH AN AUDIO SIGNAL PRESENTED TO A COCHLEAR IMPLANT PATIENT

(71) Applicant: ADVANCED BIONICS AG, Staefa (CH)

(72) Inventors: Adam B. Strauss, Santa Monica, CA (US); Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/079,036

(22) Filed: Mar. 23, 2016

(65) Prior Publication Data

US 2016/0277849 A1 Sep. 22, 2016

Related U.S. Application Data

(63) Continuation of application No. 14/375,321, filed as application No. PCT/US2013/023099 on Jan. 25, 2013, now Pat. No. 9,324,339.

(60) Provisional application No. 61/592,095, filed on Jan. 30, 2012.

(51) Int. Cl.
*H04R 25/00* (2006.01)
*G10L 25/93* (2013.01)

(52) U.S. Cl.
CPC ............ *H04R 25/353* (2013.01); *G10L 25/93* (2013.01); *H04R 25/356* (2013.01); *H04R 2225/43* (2013.01); *H04R 2460/01* (2013.01)

(58) Field of Classification Search
None
See application file for complete search history.

(56) References Cited

U.S. PATENT DOCUMENTS

| | | | | |
|---|---|---|---|---|
| 7,171,272 B2 * | 1/2007 | Blamey | ............... | A61N 1/36032 607/57 |
| 7,286,675 B1 * | 10/2007 | O'Neill | ............... | A61N 1/36032 381/102 |
| 7,426,414 B1 * | 9/2008 | Litvak | ................ | A61N 1/36032 607/56 |

(Continued)

OTHER PUBLICATIONS

Abe, et al., "Robust Pitch Estimation with Harmonics Enhancement in Noisy Environments Based on Instantaneous Frequency", *Precision and Intelligence Laboratory Tokyo Institute of Technology*, Yokohama, Japan.

(Continued)

*Primary Examiner* — Marcus T Riley
(74) *Attorney, Agent, or Firm* — ALG Intellectual Property, LLC

(57) ABSTRACT

An exemplary sound processor 1) identifies at least one frequency bin, included in a plurality of frequency bins included in a frequency spectrum of an audio signal that is presented to a cochlear implant patient, that contains spectral energy above a modified spectral envelope, 2) identifies each frequency bin that contains spectral energy below the modified spectral envelope, 3) enhances the spectral energy contained in the at least one frequency bin identified as containing spectral energy above the modified spectral envelope, and 4) compresses the spectral energy contained in each frequency bin identified as containing spectral energy below the modified spectral envelope.

20 Claims, 10 Drawing Sheets

(56) References Cited

U.S. PATENT DOCUMENTS

| | | | | |
|---|---|---|---|---|
| 8,135,152 B2* | 3/2012 | Swanson | ............... | G11C 27/02 381/312 |
| 8,401,657 B1* | 3/2013 | Litvak | ............... | A61N 1/36032 607/55 |
| 8,467,881 B2* | 6/2013 | Saoji | ............... | A61N 1/36032 607/55 |
| 9,324,339 B2* | 4/2016 | Strauss | ............. | A61N 1/36032 |
| 2005/0107843 A1* | 5/2005 | McDermott | ....... | A61N 1/36032 607/57 |
| 2006/0080087 A1* | 4/2006 | Vandali | ............. | A61N 1/36032 704/207 |
| 2006/0100672 A1* | 5/2006 | Litvak | ............... | A61N 1/36032 607/57 |
| 2009/0024185 A1* | 1/2009 | Kulkarni | ........... | A61N 1/36032 607/57 |
| 2009/0226015 A1* | 9/2009 | Zeng | ................... | H04R 25/353 381/316 |
| 2010/0246837 A1* | 9/2010 | Krause | ................... | G10L 15/00 381/58 |
| 2010/0249880 A1* | 9/2010 | Aschbacher | ....... | A61N 1/36032 607/57 |
| 2011/0286618 A1* | 11/2011 | Vandali | ............. | A61N 1/36032 381/320 |
| 2013/0023955 A1* | 1/2013 | Schleich | ........... | A61N 1/36032 607/57 |
| 2013/0023967 A1* | 1/2013 | Stafford | ............... | A61N 5/0622 607/89 |
| 2015/0057998 A1* | 2/2015 | Strauss | ............. | A61N 1/36032 704/207 |

OTHER PUBLICATIONS

International Search Report and Written Opinion received in International Application No. PCT/US13/023099, dated Apr. 17, 2013.
Non-Final Office Action received in U.S. Appl. No. 14/375,321 dated Oct. 6, 2015.

* cited by examiner

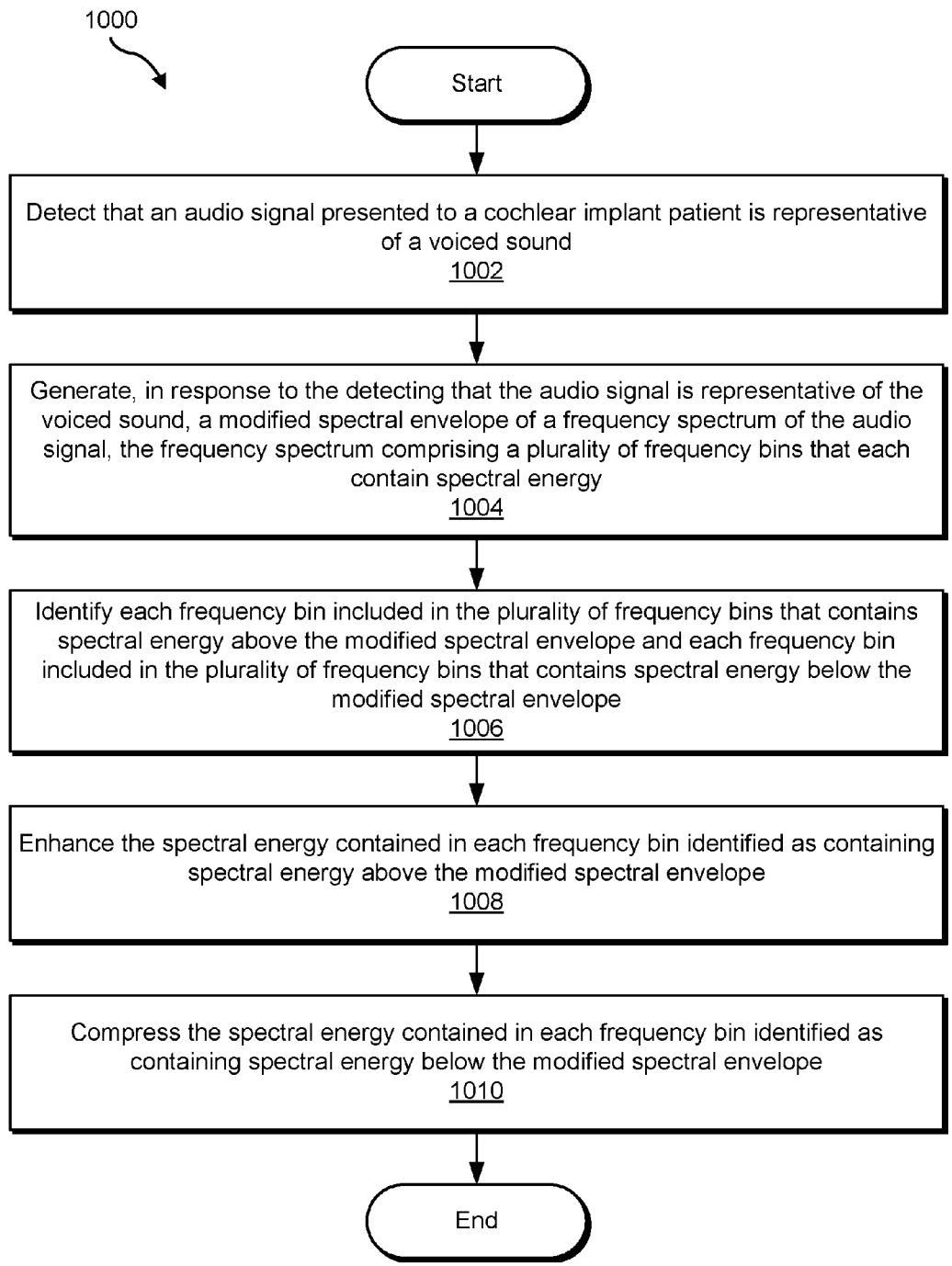

METHODS AND SYSTEMS FOR ENHANCING PITCH ASSOCIATED WITH AN AUDIO SIGNAL PRESENTED TO A COCHLEAR IMPLANT PATIENT

RELATED APPLICATIONS

The present application is a continuation application of U.S. patent application Ser. No. 14/375,321, filed Jul. 29, 2014, which application is a U.S. National Stage Entry of PCT Application No. PCT/US2013/023099, filed Jan. 25, 2013, which application claims the benefit of U.S. Provisional Patent Application No. 61/592,095, filed Jan. 30, 2012. These applications are incorporated herein by reference in their respective entireties.

BACKGROUND INFORMATION

Speech often includes a number of dominant and secondary pitches that convey the various sounds included in the speech. For example, a particular voiced sound may include a dominant pitch and a number of harmonic components produced by vibration of the vocal cords. Unfortunately, background noise interferes with the ability of many cochlear implant patients to recognize these pitches. Hence, many cochlear implant patients have difficulty understanding speech in noisy environments.

Various cochlear implant systems alleviate this problem to some degree by using noise reduction techniques configured to reduce the amount of noise contained in audio signals presented to cochlear implant patients. Additional improvements in speech perception may be made by enhancing the dominant and secondary pitches included an audio signal presented to a cochlear implant patient. This is typically done by detecting spectral peaks included in a frequency spectrum of the audio signal, identifying each spectral peak that is associated with a dominant or secondary pitch, and then enhancing the identified spectral peaks. Unfortunately, this process can be computationally intensive and error prone.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 10 illustrates another exemplary method of enhancing pitch associated with an audio signal presented to a cochlear implant patient according to principles described herein.

DETAILED DESCRIPTION

Figure 1:
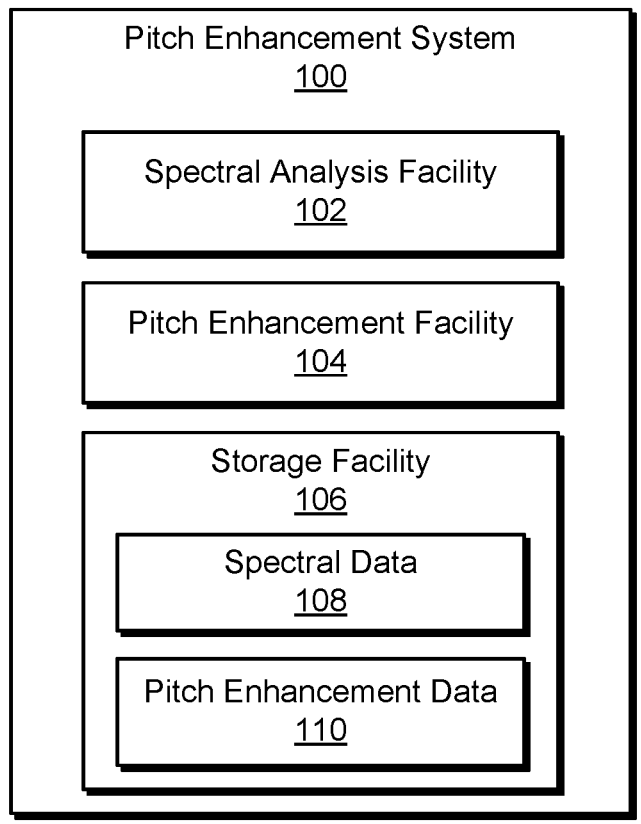
FIG. 1 illustrates an exemplary pitch enhancement system according to principles described herein.

Methods and systems for enhancing pitch associated with an audio signal presented to a cochlear implant patient are described herein. As will be described below, a pitch enhancement system may 1) determine a frequency spectrum of an audio signal presented to a patient, the frequency spectrum comprising a plurality of frequency bins that each contain spectral energy, 2) generate a modified spectral envelope of the frequency spectrum of the audio signal, 3) identify each frequency bin included in the plurality of frequency bins that contains spectral energy above the modified spectral envelope and each frequency bin included in the plurality of frequency bins that contains spectral energy below the modified spectral envelope, 4) enhance the spectral energy contained in each frequency bin identified as containing spectral energy above the modified spectral envelope, and 5) compress the spectral energy contained in each frequency bin identified as containing spectral energy below the modified spectral envelope.

By enhancing the spectral energy contained in all of the frequency bins identified as containing spectral energy above the modified spectral envelope and compressing the spectral energy contained in all of the frequency bins identified as containing spectral energy below the modified spectral envelope, the dominant and secondary pitches associated with the audio signal presented to the patient may be enhanced (thereby improving perception by a cochlear implant patient of the dominant and secondary pitches) without having to specifically identify each spectral peak included in the frequency spectrum of the audio signal that is representative of a dominant or secondary pitch. Hence, the pitch enhancement methods and systems described herein are relatively more computationally efficient, accurate, and effective than conventional techniques used to enhance pitch.

In some examples, the methods and systems described herein may be used to improve speech perception by a cochlear implant patient. For example, the pitch enhancement system may be further configured to determine whether an audio signal presented to a cochlear implant patient is representative of a voiced sound or of an unvoiced sound. "Voiced sounds" (e.g., vowels) may include a dominant pitch and a number of harmonic components produced by vibration of the vocal cords. "Unvoiced sounds" (e.g., some consonants) do not have a dominant pitch and/or any harmonic structure. Hence, if the pitch enhancement system determines that the audio signal is representative of a voiced sound, the pitch enhancement system may perform the enhancing and compressing of the spectral energy contained in the various frequency bins of the audio signal as described above (which may be referred to generally herein as applying a pitch enhancement heuristic to the audio signal). However, if the pitch enhancement system determines that the audio signal is instead representative of an unvoiced sound, the pitch enhancement system may abstain from applying the pitch enhancement heuristic to the audio signal. By selectively applying the pitch enhancement heuristic to voiced sounds only, processing resources may be conserved and overall performance of the pitch enhancement system may be optimized.

The methods and systems described herein may be used to enhance pitch associated with an audio signal presented to any type of cochlear implant patient as may serve a particular implementation. For example, as will be described below, the methods and systems described herein may be applied to unilateral cochlear implant patients (i.e., patients fitted with a single cochlear implant), bilateral cochlear implant patients (i.e., patients fitted with separate cochlear implants for each ear), bimodal cochlear implant patients (i.e., patients fitted with a cochlear implant for one ear and an acoustic hearing instrument for the other ear), electro-acoustic stimulation ("EAS") patients (i.e., patients fitted with an EAS device configured to provide both electrical and acoustic stimulation), and/or hearing aid patients.

FIG. 1 illustrates an exemplary pitch enhancement system 100 ("system 100"). As shown, system 100 may include, without limitation, a spectral analysis facility 102, a pitch enhancement facility 104, and a storage facility 106 communicatively coupled to one another. One or more of facilities 102-106 may include one or more computing devices and/or processors configured to perform one or more of the functions described herein. Facilities 102-106 will now be described in more detail.

Spectral analysis facility 102 may be configured to determine (e.g., compute) a frequency spectrum of an audio signal presented to a patient. This may be performed in any suitable manner. For example, spectral analysis facility 102 may apply a Discrete Fourier Transform (e.g., a high resolution Fast Fourier Transform ("FFT")) to the audio signal.

In some examples, spectral analysis facility 102 may minimize computational complexity by computing the frequency spectrum for only those frequencies that are less than a predetermined threshold frequency. For example, voiced sounds are typically focused at relatively lower frequencies (e.g., at frequencies that are less than 2000 Hz) than unvoiced sounds. Hence, spectral analysis facility 102 may limit the range for which the frequency spectrum of the audio signal is computed to those frequencies that are less than 2000 Hz.

Figure 2:
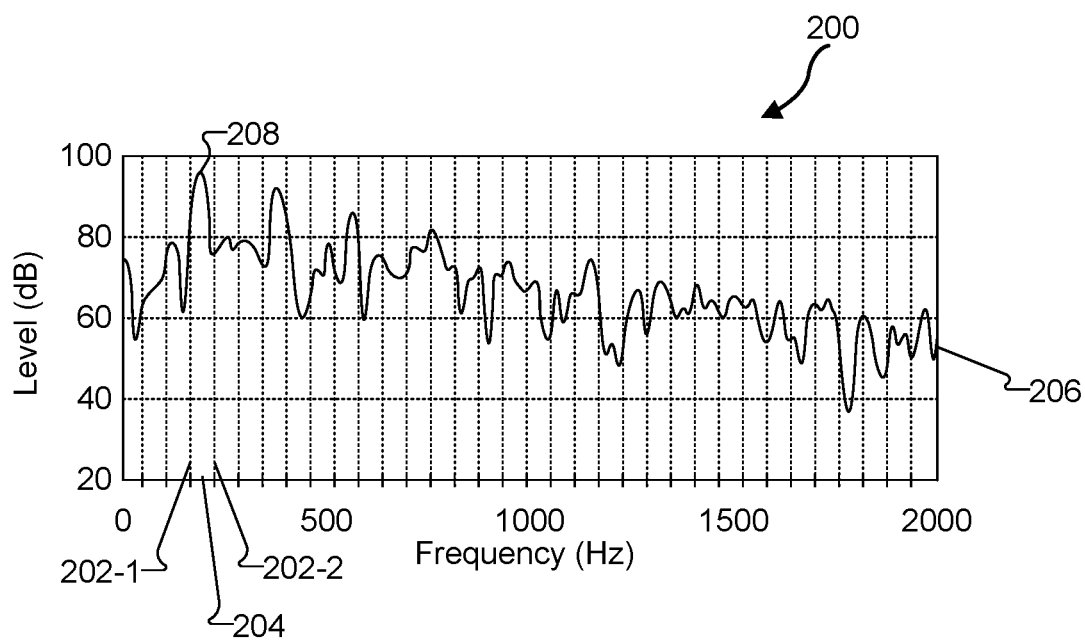
FIG. 2 illustrates an exemplary frequency spectrum of an audio signal that may be presented to a cochlear implant patient according to principles described herein.

FIG. 2 illustrates an exemplary frequency spectrum 200 of an audio signal that may be presented to a cochlear implant patient. Frequency spectrum 200 spans a frequency range of zero to 2000 Hz for illustrative purposes only. It will be recognized that frequency spectrum 200 may alternatively span a frequency range of any other size as may serve a particular implementation.

As illustrated by the vertical dashed lines in FIG. 2, frequency spectrum 200 may include or be divided into a plurality of frequency bins each having any suitable bandwidth as may serve a particular implementation. To illustrate, vertical dashed lines 202-1 and 202-2 define a particular frequency bin labeled 204. In some examples, the number of frequency bins included in frequency spectrum 200 depends on the resolution of the Discrete Fourier Transform applied to the audio signal.

Curve 206 is representative of a spectral energy distribution across the various frequency bins included in frequency spectrum 200. For example, FIG. 2 shows that frequency bin 204 contains a spectral energy peak 208. In the example of FIG. 2, spectral energy peak 208 is representative of a dominant pitch associated with a voiced segment.

Returning to FIG. 1, spectral analysis facility 102 may be further configured to generate a modified spectral envelope of frequency spectrum of the audio signal. As used herein, a "modified spectral envelope" of a frequency spectrum of an audio signal refers to a spectral envelope that has been smoothed and/or otherwise modified such that one or more spectral peaks included in the frequency spectrum and representative of one or more dominant and/or secondary pitches are above (i.e., have higher spectral energies than) the modified spectral envelope.

Figure 3:
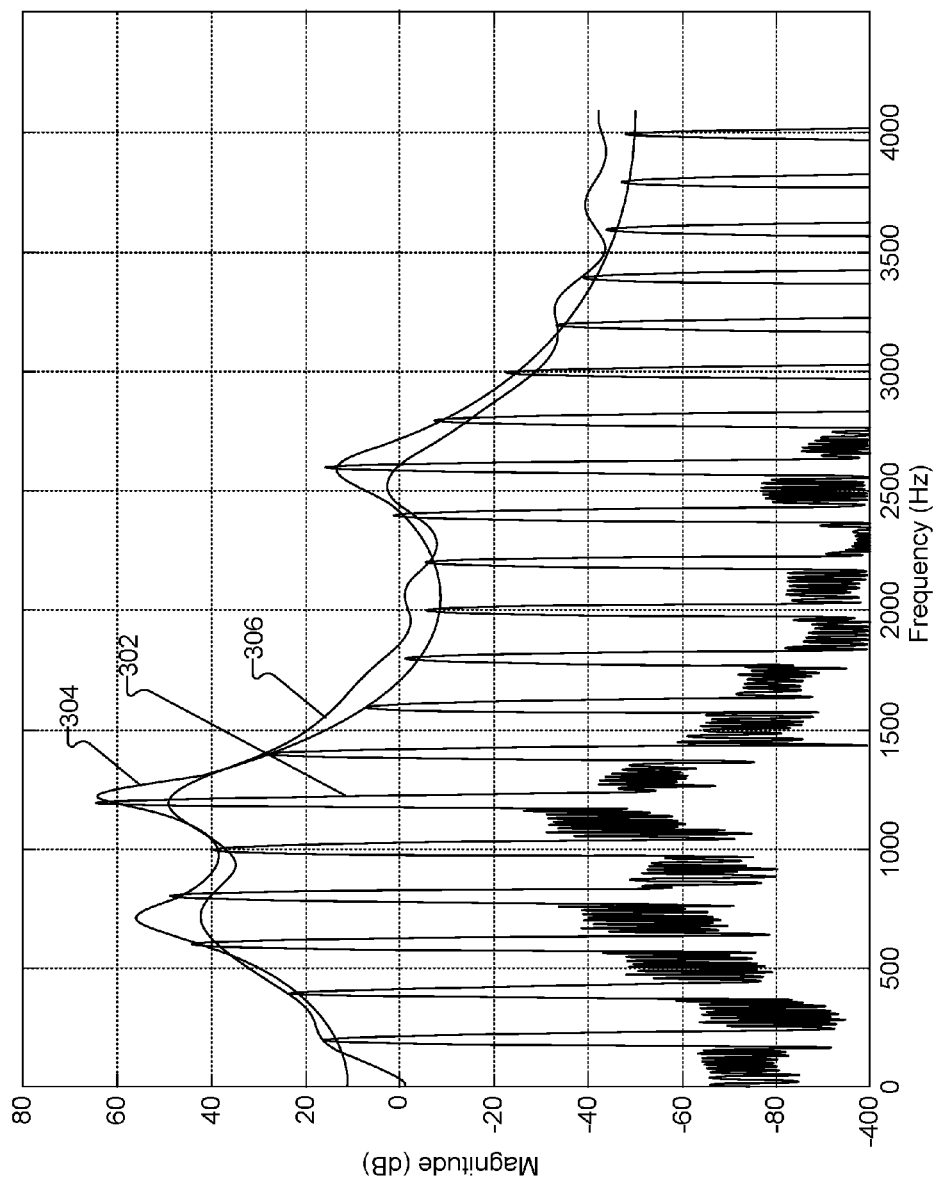
FIG. 3 illustrates an exemplary frequency spectrum, spectral envelope, and modified spectral envelope according to principles described herein.

To illustrate, FIG. 3 shows an exemplary frequency spectrum 300 of an audio signal representative of the synthetic "ah" vowel sound. Curve 302 is representative of a spectral energy distribution of the audio signal with frequency spectrum 300, curve 304 is representative of a spectral envelope of frequency spectrum 300, and curve 306 is representative of a modified spectral envelope 306 of frequency spectrum 300. As shown, spectral envelope 304 describes the envelope of the frequency spectrum 300 by wrapping around and linking the various spectral peaks included in frequency spectrum 300. Modified spectral envelope 306 has been smoothed such that various spectral peaks included in the frequency spectrum 300 are above the modified spectral envelope 306.

Spectral analysis facility 102 may be configured to generate a modified spectral envelope (e.g., modified spectral envelope 306) of an audio signal in any suitable manner. For example, spectral analysis facility 102 may utilize a cepstral windowing heuristic to generate the modified spectral envelope. This may include, for example, computing the log-magnitude spectrum of the audio signal, performing the inverse FFT to obtain a real cepstrum, lowpass-windowing the cepstrum, and performing an FFT on the lowpass-windowed cepstrum to obtain a smoothed log-magnitude spectrum of the audio signal. Various parameters associated with the cepstral windowing heuristic may be adjusted to adjust the amount of smoothing that is performed to generate the modified spectral envelope as may serve a particular implementation.

Figure 4:
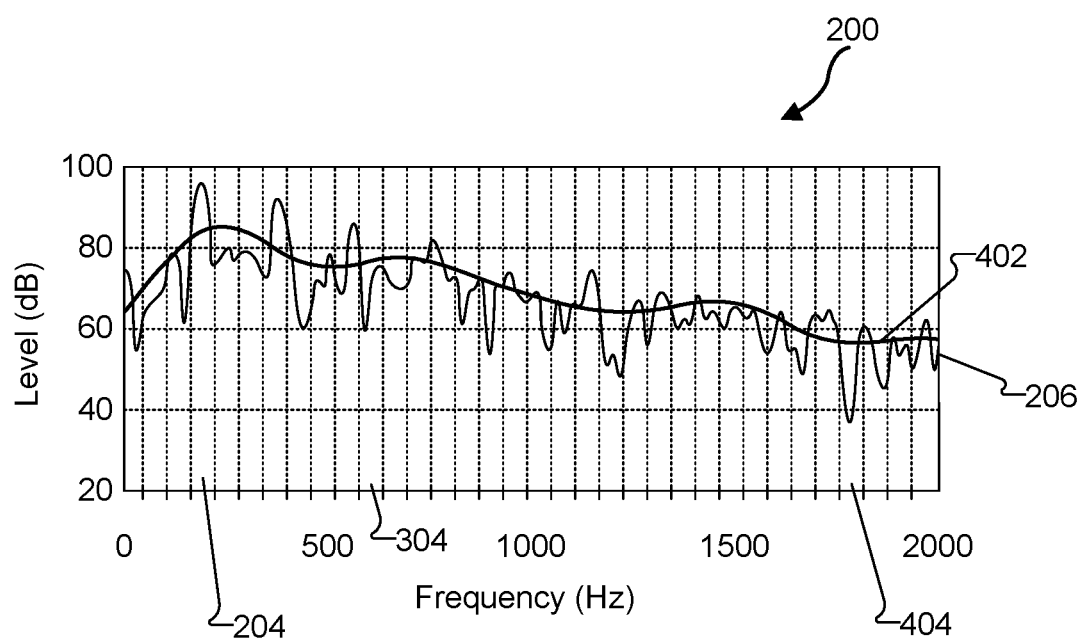
FIG. 4 illustrates an exemplary modified spectral envelope that may be generated for the audio signal represented in FIG. 2 according to principles described herein.

To further illustrate the concept of a modified spectral envelope, FIG. 4 illustrates an exemplary modified spectral envelope 402 that may be generated for the audio signal represented in FIG. 2. Modified spectral envelope 402 is shown in FIG. 4 to be superimposed on the spectral energy distribution curve 206 for illustrative purposes only. As shown, spectral energy distribution curve 206 includes various spectral peaks that are above the modified spectral envelope 402. As will be described below, this may allow system 100 to compare spectral energy distribution curve 206 to modified spectral envelope 402 to determine which frequency bins contain spectral energy that is to be enhanced and which frequency bins contain spectral energy that is to be compressed.

Returning to FIG. 1, pitch enhancement facility 104 may be configured to perform various pitch enhancement operations associated with an audio signal presented to a patient. For example, once spectral analysis facility 102 has determined a frequency spectrum of an audio signal presented to a cochlear implant patient and generated a modified spectral envelope of the frequency spectrum, pitch enhancement facility 104 may identify each frequency bin included in the frequency spectrum that contains spectral energy above the modified spectral envelope and each frequency bin included in the frequency spectrum that contains spectral energy below the modified spectral envelope. This may be performed in any suitable manner.

To illustrate, reference is again made to FIG. 4. As shown in FIG. 4, a frequency bin may be identified as containing spectral energy above modified spectral envelope 402 if the portion of spectral energy distribution curve 206 associated with the frequency bin (i.e., the portion of spectral energy distribution curve 206 that passes through the frequency bin) has a higher gain level than that of the portion of modified spectral envelope 402 associated with the frequency bin. An example of a frequency bin that contains spectral energy above modified spectral envelope 402 is frequency bin 204.

Likewise, a frequency bin may be identified as containing spectral energy below modified spectral envelope 402 if the portion of spectral energy distribution curve 206 associated with the frequency bin has a lower gain level than that of the portion of modified spectral envelope 402 associated with the frequency bin. An example of a frequency bin that contains spectral energy below modified spectral envelope 402 is frequency bin 404.

The gain level of spectral energy contained in a particular frequency bin may be determined in any suitable manner. For example, the gain level of spectral energy contained in a particular frequency bin may be determined by averaging (e.g., smoothing) all of the spectral energy contained within the frequency bin. In an alternative embodiment, the gain level of spectral energy contained in a particular frequency bin may set to be equal to a maximum or minimum gain level of spectral energy contained in the frequency bin.

Likewise, the gain level of the portion of modified spectral envelope 402 that corresponds to a particular frequency bin may be determined in any suitable manner. For example, the gain level of the portion of modified spectral envelope 402 that corresponds to a particular frequency bin may be determined by averaging the various gain levels of modified spectral envelope 402 associated with the frequency bin.

Hence, in situations where a particular frequency bin contains spectral energy both above and below modified spectral envelope 402 (e.g., frequency bin 406), pitch enhancement facility 104 may be configured to identify the frequency bin as containing spectral energy above or below modified spectral envelope 402 by comparing an average gain level (or, in some alternative embodiments, a maximum or minimum gain level) of spectral energy contained in the frequency bin to the average gain level of the portion of modified spectral envelope 402 associated with that frequency bin.

Pitch enhancement facility 104 may be further configured to apply a pitch enhancement heuristic to the audio signal by enhancing the spectral energy contained in each frequency bin identified as containing spectral energy above the modified spectral envelope and compressing the spectral energy contained in each frequency bin identified as containing spectral energy below the modified spectral envelope. The enhancement and compression may be performed in any suitable manner.

Figure 5:
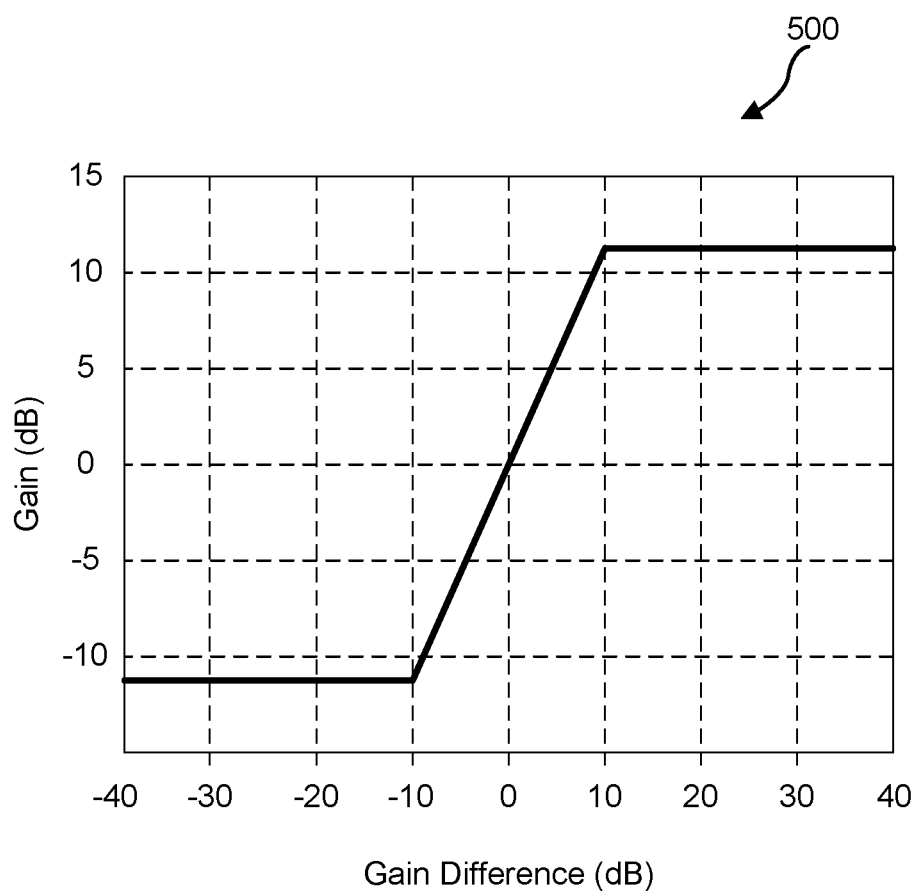
FIG. 5 illustrates an exemplary gain function that may be used to enhance and compress the spectral energy contained in the various frequency bins included in a frequency spectrum of an audio signal according to principles described herein.

For example, the enhancement and compression may be performed in accordance with a predetermined gain function. FIG. 5 illustrates an exemplary gain function 500 that may be used to enhance and compress the spectral energy contained in the various frequency bins included in a frequency spectrum of an audio signal. As shown, if the gain difference between the spectral energy contained in a particular frequency bin and the portion of the modified spectral envelope corresponding to the bin is positive (i.e., greater than zero), pitch enhancement facility 104 may enhance the spectral energy contained in the frequency bin by applying a positive gain to the spectral energy contained in the frequency bin. Conversely, if the gain difference between the spectral energy contained in a particular frequency bin and the portion of the modified spectral envelope corresponding to the bin is negative (i.e., less than zero), pitch enhancement facility 104 may compress the spectral energy contained in the frequency bin by applying a negative gain to the spectral energy contained in the frequency bin.

To illustrate, if the gain difference corresponding to a particular frequency bin is 10 dB or higher, a gain of 12 dB is applied to the spectral energy contained within the frequency bin in accordance with gain function 500. If the gain difference corresponding to a particular frequency bin is −10 dB or lower, a gain of −12 dB is applied to the spectral energy contained within the frequency bin in accordance with gain function 500. If the gain difference corresponding to a particular frequency bin is between −10 dB and 10 dB (i.e., the linear region of gain function 510), a gain of 1.2 dB per multiplication (i.e., the slope of gain function 510 within the linear region) is applied to the spectral energy contained within the frequency bin in accordance with gain function 500. It will be recognized that gain function 500 is merely illustrative of the many different gain functions that may be used in accordance with the methods and systems described herein.

In some examples, pitch enhancement facility 104 may be configured to selectively apply the pitch enhancement heuristic to only those audio signals that are representative of voiced sounds (as opposed to unvoiced sounds). To this end, pitch enhancement facility 104 may be configured to detect whether a particular audio signal presented to a cochlear implant patient is representative of a voiced sound or whether the audio signal is representative of an unvoiced sound. This may be performed in any suitable manner using any suitable signal processing techniques as may serve a particular implementation. If pitch enhancement facility 104 determines that a particular audio signal is representative of a voiced sound, pitch enhancement 104 may proceed to apply the pitch enhancement heuristic to the audio signal. However, if pitch enhancement facility 104 determines that the audio signal is instead representative of an unvoiced sound, pitch enhancement 104 may abstain from applying the pitch enhancement heuristic to the audio signal. As mentioned, by selectively applying the pitch enhancement heuristic to voiced sounds only, processing resources may be conserved and overall performance of system 100 may be optimized.

In some examples, pitch enhancement facility 104 may be further configured to apply a noise reduction heuristic to the audio signal. By applying both a noise reduction heuristic and a pitch enhancement heuristic (in any suitable order) to the audio signal, overall performance of system 100 may be further optimized. Any suitable noise reduction heuristic may be applied to the audio signal as may serve a particular implementation.

Returning to FIG. 1, storage facility 106 may be configured to maintain spectral data 108 generated and/or used by spectral analysis facility 102 and/or pitch enhancement data 110 generated and/or used by pitch enhancement facility 104. It will be recognized that storage facility 106 may maintain additional or alternative data as may serve a particular implementation.

As mentioned, the methods and systems described herein may be used to enhance pitch associated with an audio signal presented to any type of cochlear implant patient. To illustrate, FIGS. 6-7 show various implementations of system 100 that may be used to enhance pitch associated with an audio signal presented to various types of cochlear implant patients.

Figure 6:
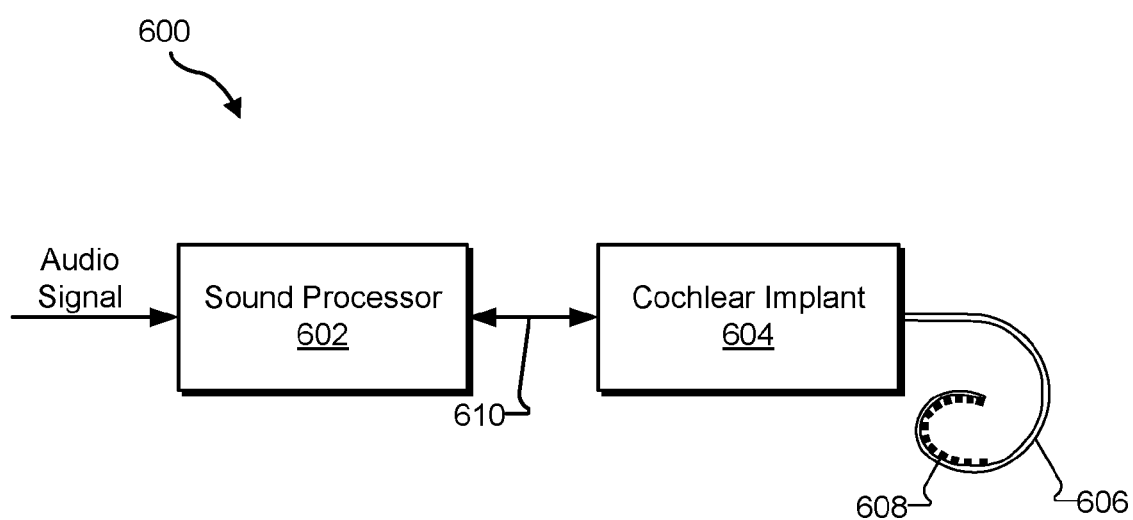
FIG. 6 illustrates an exemplary implementation of the system of FIG. 1 wherein the cochlear implant patient is fitted with a cochlear implant according to principles described herein.
Figure 7:
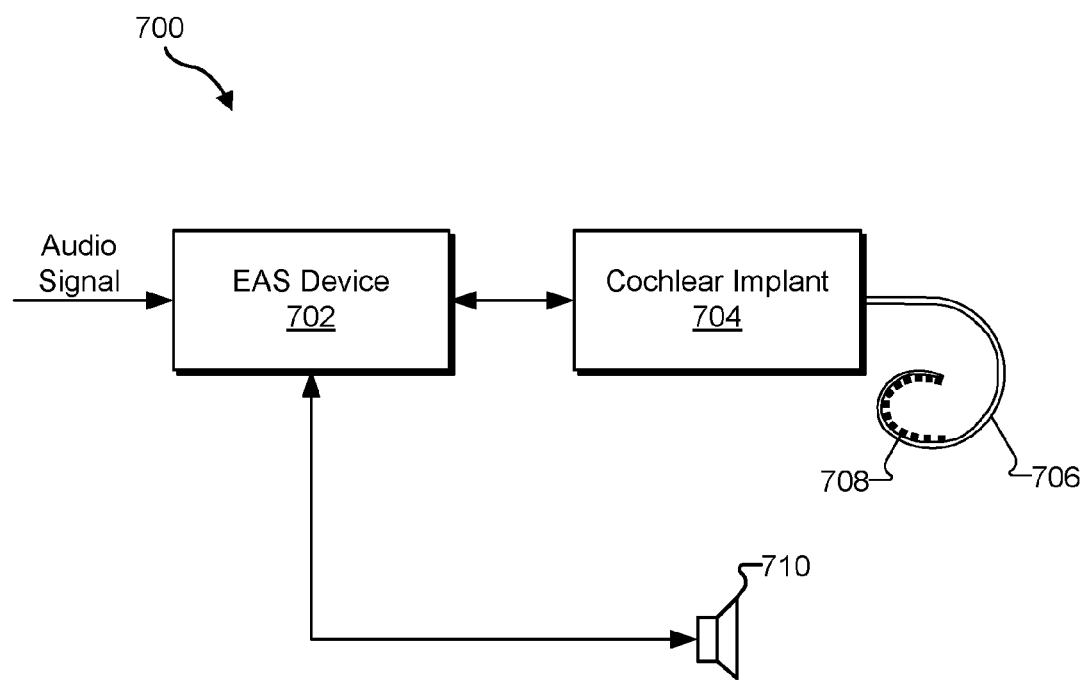
FIG. 7 illustrates an exemplary implementation of the system of FIG. 1 wherein the cochlear implant patient is fitted with an electro-acoustic stimulation system according to principles described herein.

FIG. 6 illustrates an exemplary implementation 600 of system 100 wherein the cochlear implant patient is fitted with a cochlear implant. As shown, implementation 600 may include a sound processor 602, a cochlear implant 604, and an electrode lead 606 having a plurality of electrodes 608 disposed thereon.

Sound processor 602 may include any suitable device configured to process an audio signal presented to a cochlear implant patient and/or control an operation of cochlear implant 604. In some examples, sound processor 602 is implemented by an externally worn unit (e.g., a behind-the-ear device, a body worn device, etc.). Alternatively, sound processor 602 may be configured to be at least partially implanted within the patient.

Cochlear implant 604 may include any suitable auditory prosthesis configured to be at least partially implanted within a patient as may serve a particular implementation. For example, cochlear implant 604 may include an implantable cochlear stimulator, a brainstem implant and/or any other type of auditory prosthesis. Sound processor 602 and cochlear implant 604 may communicate by way of communication channel 610, which may be wired or wireless as may serve a particular implementation.

Electrode lead 606 may be implanted within the patient such that electrodes 608 are in communication with stimulation sites within the cochlea and/or anywhere else along the auditory pathway of the patient. In this configuration, sound processor 602 may direct cochlear implant 604 to apply electrical stimulation representative of an audio signal to one or more stimulation sites within the patient by way of one or more of electrodes 608.

In some examples, system 100 may be implemented by sound processor 602. For example, sound processor 602 may enhance spectral energy contained in one more frequency bins included in a frequency spectrum of an audio signal and compress spectral energy contained in one or more other frequency bins included in the frequency spectrum, as described above. Sound processor 602 may then direct cochlear implant 604 to apply electrical stimulation representative of the enhanced spectral energy and the compressed spectral energy to one or more stimulation sites within the patient by way of one or more of electrodes 608. By so doing, the clarity of speech, music, and/or other types of audio signals as perceived by the cochlear implant patient may be optimized.

FIG. 7 illustrates an exemplary implementation 700 of system 100 wherein the cochlear implant patient is fitted with an EAS system. As shown, implementation 700 may include an EAS device 702, a cochlear implant 704, an electrode lead 706 having a plurality of electrodes 708 disposed thereon, and a loudspeaker 710.

EAS device 702 may be configured to provide electrical and acoustic stimulation to the same ear (or to alternate ears) and may be used when the cochlear implant patient has some residual some hearing in the low frequencies (e.g., below 1000 Hz) and severe hearing loss in the high frequencies (e.g., above 1000 Hz). To this end, EAS device 702 may be configured to direct cochlear implant 704 (which may be similar to cochlear implant 604 described above) to apply electrical stimulation representative of audio content included in a relatively high frequency band (e.g., above 1000 Hz) to one or more stimulation sites within the patient by way of electrodes 708 and to direct loudspeaker 710 to apply acoustic stimulation representative of audio content included in a relatively low frequency band (e.g., below 1000 Hz) to the patient.

In some examples, system 100 may be implemented by EAS device 702. For example, EAS device 702 may enhance spectral energy contained in one more frequency bins included in a frequency spectrum of a relatively low frequency audio signal (e.g., a voiced sound) and compress spectral energy contained in one or more other frequency bins included in the frequency spectrum, as described above. EAS device 702 may then direct loudspeaker 710 to apply acoustic stimulation representative of the enhanced spectral energy and the compressed spectral energy to the patient. By so doing, the patient may more effectively perceive the pitch of the audio signal.

Figure 8:
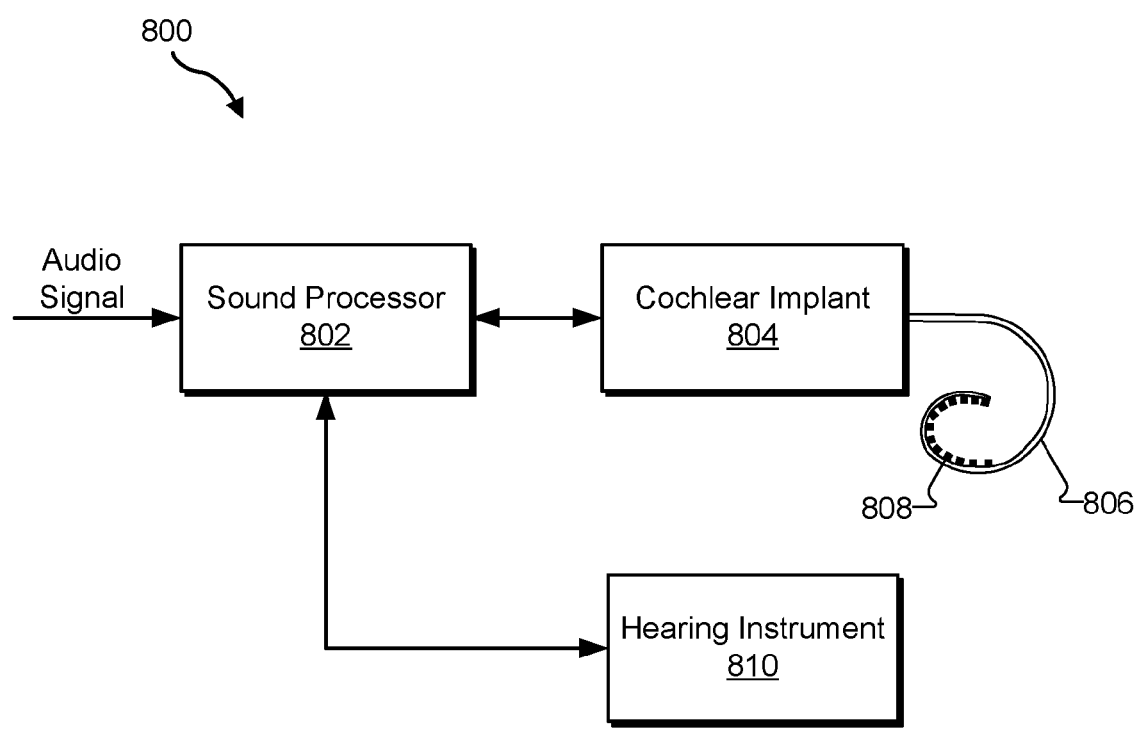
FIG. 8 illustrates an exemplary implementation of the system of FIG. 1 wherein the cochlear implant patient is fitted with a bimodal cochlear implant system according to principles described herein.

FIG. 8 illustrates an exemplary implementation 800 of system 100 wherein the cochlear implant patient is fitted with a bimodal cochlear implant system. As shown, implementation 800 is similar to implementation 600 in that it includes a sound processor 802, a cochlear implant 804, and an electrode lead 806 having a plurality of electrodes 808 disposed thereon. However, implementation also shows a hearing instrument 810 communicatively coupled to sound processor 802. Hearing instrument 810 may include any type of acoustic hearing aid as may serve a particular implementation.

Implementation 800 may be used for a bimodal cochlear implant patient. For example, cochlear implant 804 may be used to apply electrical stimulation to one of the ears of the patient and hearing instrument 810 may be used to apply acoustic stimulation to the other ear of the patient. This arrangement may be beneficial when the patient has residual hearing in one ear but not the other.

In some examples, system 100 may be implemented by sound processor 802 and/or hearing instrument 810. For example, sound processor 802 may enhance spectral energy contained in one more frequency bins included in a frequency spectrum of a relatively low frequency audio signal (e.g., a voiced sound) and compress spectral energy contained in one or more other frequency bins included in the frequency spectrum, as described above. Sound processor 802 may then direct hearing instrument 810 to apply acoustic stimulation representative of the enhanced spectral energy and the compressed spectral energy to the patient. Alternatively, hearing instrument 810 may perform the enhancement and/or compression. By so doing, the patient may more effectively perceive the pitch of the audio signal.

Figure 9:
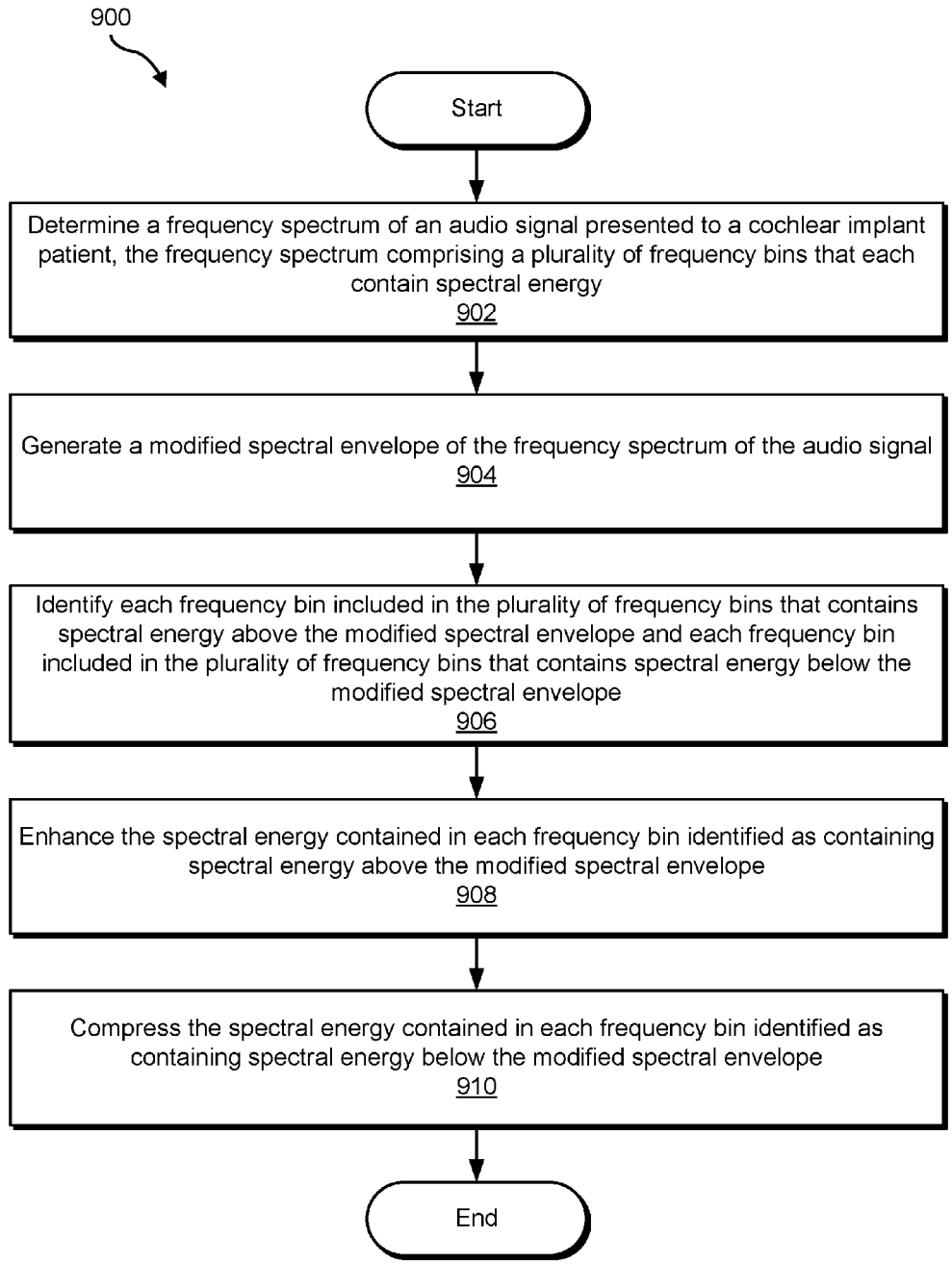
FIG. 9 illustrates an exemplary method of enhancing pitch associated with an audio signal presented to a cochlear implant patient according to principles described herein.

FIG. 9 illustrates an exemplary method 900 of enhancing pitch associated with an audio signal presented to a cochlear implant patient. While FIG. 9 illustrates exemplary steps according to one embodiment, other embodiments may omit, add to, reorder, and/or modify any of the steps shown in FIG. 9. One or more of the steps shown in FIG. 9 may be performed by system 100 and/or any implementation thereof.

In step 902, a pitch enhancement system determines a frequency spectrum of an audio signal presented to a cochlear implant patient. As described above, the frequency spectrum includes a plurality of frequency bins that each contain spectral energy. Step 902 may be performed in any of the ways described herein.

In step 904, the pitch enhancement system generates a modified spectral envelope of the frequency spectrum of the audio signal. Step 904 may be performed in any of the ways described herein.

In step 906, the pitch enhancement system identifies each frequency bin included in the plurality of frequency bins that contains spectral energy above the modified spectral envelope and each frequency bin included in the plurality of frequency bins that contains spectral energy below the modified spectral envelope. Step 906 may be performed in any of the ways described herein.

In step 908, the pitch enhancement system enhances the spectral energy contained in each frequency bin identified as containing spectral energy above the modified spectral envelope. Step 908 may be performed in any of the ways described herein.

In step 910, the pitch enhancement system compresses the spectral energy contained in each frequency bin identified as containing spectral energy below the modified spectral envelope. Step 910 may be performed in any of the ways described herein.

FIG. 10 illustrates another exemplary method 1000 of enhancing pitch associated with an audio signal presented to a cochlear implant patient. While FIG. 10 illustrates exemplary steps according to one embodiment, other embodiments may omit, add to, reorder, and/or modify any of the steps shown in FIG. 10. One or more of the steps shown in FIG. 10 may be performed by system 100 and/or any implementation thereof.

In step 1002, a pitch enhancement system detect that an audio signal presented to a cochlear implant patient is representative of a voiced sound. Step 1002 may be performed in any of the ways described herein.

In step 1004, the pitch enhancement system generates, in response to the detecting that the audio signal is representative of the voiced sound, a modified spectral envelope of a frequency spectrum of the audio signal, the frequency spectrum comprising a plurality of frequency bins that each contain spectral energy. Step 1004 may be performed in any of the ways described herein.

In step 1006, the pitch enhancement system identifies each frequency bin included in the plurality of frequency bins that contains spectral energy above the modified spectral envelope and each frequency bin included in the plurality of frequency bins that contains spectral energy below the modified spectral envelope. Step 1006 may be performed in any of the ways described herein.

In step 1008, the pitch enhancement system enhances the spectral energy contained in each frequency bin identified as containing spectral energy above the modified spectral envelope. Step 1008 may be performed in any of the ways described herein.

In step 1010, the pitch enhancement system compresses the spectral energy contained in each frequency bin identified as containing spectral energy below the modified spectral envelope. Step 1010 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a sound processor that
   identifies at least one frequency bin, included in a plurality of frequency bins included in a frequency spectrum of an audio signal that is presented to a cochlear implant patient, that contains spectral energy above a modified spectral envelope of the frequency spectrum of the audio signal,
   identifies each frequency bin included in the plurality of frequency bins that contains spectral energy below the modified spectral envelope,
   enhances the spectral energy contained in the at least one frequency bin identified as containing spectral energy above the modified spectral envelope by applying a positive gain to the spectral energy contained in the at least one frequency bin identified as containing spectral energy above the modified spectral envelope, and
   compresses the spectral energy contained in each frequency bin identified as containing spectral energy below the modified spectral envelope by applying a negative gain to the spectral energy contained in each frequency bin identified as containing spectral energy below the modified spectral envelope.

2. The system of claim 1, wherein the sound processor enhances the spectral energy contained in the at least one frequency bin identified as containing spectral energy above the modified spectral envelope and compresses the spectral energy contained in each frequency bin identified as containing spectral energy below the modified spectral envelope in accordance with a predetermined gain function.

3. The system of claim 1, wherein the patient is fitted with a cochlear implant, and wherein the sound processor directs the cochlear implant to apply electrical stimulation representative of the enhanced spectral energy and the compressed spectral energy to one or more stimulation sites within the patient.

4. The system of claim 1, wherein the patient is fitted with an electro-acoustic stimulation system, and wherein the sound processor directs a loudspeaker included in the electro-acoustic stimulation system to apply acoustic stimulation representative of the enhanced spectral energy and the compressed spectral energy to the patient.

5. The system of claim 1, wherein the patient is fitted with a cochlear implant for a first ear of the patient and a hearing device for a second ear of the patient, and wherein the sound processor directs the hearing device to apply acoustic stimulation representative of the enhanced spectral energy and the compressed spectral energy to the second ear of the patient.

6. The system of claim 1, wherein the sound processor determines the frequency spectrum of the audio signal by determining the frequency spectrum of the audio signal for only those frequencies that are less than a predetermined threshold frequency.

7. The system of claim 6, wherein the predetermined threshold frequency is 2000 Hertz.

8. The system of claim 1, wherein the audio signal is representative of a voiced sound.

9. The system of claim 1, wherein the sound processor determines the frequency spectrum by applying a Discrete Fourier Transform to the audio signal.

10. The system of claim 1, wherein the sound processor generates the modified spectral envelope by utilizing a cepstral windowing heuristic.

11. The system of claim 1, wherein the sound processor applies a noise reduction heuristic to the audio signal.

12. A system comprising:
a sound processor that
detects that an audio signal presented to a cochlear implant patient is representative of a voiced sound, and
generates, in response to the detecting that the audio signal is representative of the voiced sound, a modified spectral envelope of a frequency spectrum of the audio signal, the frequency spectrum comprising a plurality of frequency bins that each contain spectral energy,
identifies each frequency bin included in the plurality of frequency bins that contains spectral energy above the modified spectral envelope and each frequency bin included in the plurality of frequency bins that contains spectral energy below the modified spectral envelope,
enhances the spectral energy contained in each frequency bin identified as containing spectral energy above the modified spectral envelope by applying a positive gain to the spectral energy contained in each frequency bin identified as containing spectral energy above the modified spectral envelope, and
compresses the spectral energy contained in each frequency bin identified as containing spectral energy below the modified spectral envelope by applying a negative gain to the spectral energy contained in each frequency bin identified as containing spectral energy below the modified spectral envelope.

13. The system of claim 12, wherein the sound processor:
detects that an additional audio signal presented to the patient is representative of an unvoiced sound; and
abstains from enhancing and compressing spectral energy associated with the additional audio signal.

14. The system of claim 12, wherein the sound processor performs the enhancement and the compression in accordance with a predetermined gain function.

15. The system of claim 12, wherein the patient is fitted with a cochlear implant, and wherein the sound processor directs the cochlear implant to apply electrical stimulation representative of the enhanced spectral energy and the compressed spectral energy to one or more stimulation sites within the patient.

16. The system of claim 12, wherein the patient is fitted with an electro-acoustic stimulation system, and wherein the sound processor directs a loudspeaker included in the electro-acoustic stimulation system to apply acoustic stimulation representative of the enhanced spectral energy and the compressed spectral energy to the patient.

17. The system of claim 12, wherein the patient is fitted with a cochlear implant for a first ear of the patient and a hearing device for a second ear of the patient, and wherein the sound processor directs the hearing device to apply acoustic stimulation representative of the enhanced spectral energy and the compressed spectral energy to the second ear of the patient.

18. The system of claim 12, wherein the sound processor applies a noise reduction heuristic to the audio signal.

19. A method comprising:
identifying, by a sound processor, at least one frequency bin, included in a plurality of frequency bins included in a frequency spectrum of an audio signal that is presented to a cochlear implant patient, that contains spectral energy above a modified spectral envelope of the frequency spectrum of the audio signal;
identifying, by the sound processor, each frequency bin included in the plurality of frequency bins that contains spectral energy below the modified spectral envelope;
enhancing, by the sound processor, the spectral energy contained in the at least one frequency bin identified as containing spectral energy above the modified spectral envelope by applying a positive gain to the spectral energy contained in the at least one frequency bin identified as containing spectral energy above the modified spectral envelope; and
compressing, by the sound processor, the spectral energy contained in each frequency bin identified as containing spectral energy below the modified spectral envelope by applying a negative gain to the spectral energy contained in each frequency bin identified as containing spectral energy below the modified spectral envelope.

20. The method of claim 19, wherein the enhancing and compressing are performed in accordance with a predetermined gain function.

* * * * *